United States Patent [19]

Janchitraponvej et al.

[11] Patent Number: 5,417,965
[45] Date of Patent: * May 23, 1995

[54] STABLE CONDITIONING SHAMPOO HAVING A HIGH FOAM LEVEL CONTAINING A SILICONE CONDITIONER, A CATIONIC QUATERNARY ACRYLATE COPOLYMER, AN ANIONIC SURFACTANT AND POLYETHYLENEIMINE

[75] Inventors: Ben Janchitraponvej, Niles; William Brown, Flossmoor, both of Ill.

[73] Assignee: Helene Curtis, Inc., Chicago, Ill.

[*] Notice: The portion of the term of this patent subsequent to Jun. 22, 2010 has been disclaimed.

[21] Appl. No.: 62,606

[22] Filed: May 17, 1993

Related U.S. Application Data

[63] Continuation-in-part of Ser. No. 719,818, Jun. 24, 1991, Pat. No. 5,221,530.

[51] Int. Cl.$^6$ .................................................. A61K 7/075
[52] U.S. Cl. ........................... 424/70.12; 252/174.23; 252/544; 252/547; 252/DIG. 13; 424/70.16; 424/70.19
[58] Field of Search .................... 424/70, 71; 252/544, 252/547, DIG. 13, 174.23

[56] References Cited

U.S. PATENT DOCUMENTS

| | | | |
|---|---|---|---|
| 3,761,417 | 9/1973 | Parran et al. | 252/106 |
| 4,252,656 | 2/1981 | Liebowitz et al. | 252/8.8 |
| 4,381,259 | 4/1983 | Homma et al. | 252/542 |
| 4,663,158 | 5/1987 | Wolfram et al. | 424/70 |
| 4,940,576 | 7/1990 | Walsh | 424/70 |
| 5,034,218 | 7/1991 | Duvel | 424/70 |
| 5,104,645 | 4/1992 | Cardin et al. | 424/70 |
| 5,221,530 | 6/1993 | Janchitraponvej et al. | 424/70 |

OTHER PUBLICATIONS

Leaflet of Allied Colloids Inc. which is intended for general guidance in the use of their products.
Leaflet of Allied Colloids, Inc. entitled "Current Status of Salcare SC92 Product".

*Primary Examiner*—Thurman K. Page
*Assistant Examiner*—R. Harrison
*Attorney, Agent, or Firm*—Marshall, O'Toole, Gerstein, Murray & Borun

[57] ABSTRACT

A conditioning shampoo containing an anionic cleansing surfactant, in an amount of about 5% to about 65% by weight, preferably about 5% to about 25% by weight, e.g., ($C_{12}$–$C_{22}$) alkyl sulfate, and/or a long chain ($C_{12}$–$C_{22}$) partially or fully ethoxylated alkyl sulfate, and/or a long chain ($C_{12}$–$C_{22}$) alkyl sulfonate, and a combination of cationic polymers comprising (1) a cationic (protonated) polyethyleneimine in an amount of about 0.1% to about 4% by weight, preferably about 0.1% to about 1% by weight, and (2) a cationic oil-soluble, water-dispersible, cross-linked quaternary acrylate/acrylamide copolymer (Polyquaternium 32), in an amount of about 0.1% to about 20% by weight of the composition, provides excellent foaming, conditioning and stability, without settling of water-insoluble materials due to anionic-cationic complexing. The composition preferably also includes one or more silicone conditioning agents, and has extended product stability, excellent overall conditioning to human hair, particularly superior wet and dry combing properties, and unexpectedly maintains very high levels of foam.

21 Claims, No Drawings

STABLE CONDITIONING SHAMPOO HAVING A HIGH FOAM LEVEL CONTAINING A SILICONE CONDITIONER, A CATIONIC QUATERNARY ACRYLATE COPOLYMER, AN ANIONIC SURFACTANT AND POLYETHYLENEIMINE

CROSS REFERENCE TO RELATED APPLICATION

This application is a continuation-in-part of application Ser. No. 07/719,818 filed Jun. 24, 1991, now U.S. Pat. No. 5,221,530.

FIELD OF THE INVENTION

The present invention is directed to a hair conditioning shampoo composition and to a method of treating hair with the composition to provide the hair with improved wet stage and dry stage conditioning properties as well as other conditioning properties, such as softness, without residual build-up of conditioning agents on the hair. The conditioning shampoo also thoroughly cleanses the hair, while conditioning, with a cleansing detergent that develops an unexpectedly high foam level and unexpected stability containing an anionic detergent, a protonated (cationic) polyethyleneimine conditioning agent and, optionally, one or more silicone conditioning agents. More particularly, the present invention is directed to a hair conditioning shampoo composition including one or more anionic cleansing surfactants, such as ammonium lauryl sulfate or ammonium lauryl ether sulfate (ALES), a protonated polyethyleneimine, and an acrylate/acrylamide copolymer conditioning agent that is stable over extended periods of time at elevated temperature.

Surprisingly, the composition develops copious amounts of foam for a conditioning shampoo while achieving excellent conditioning benefits, and is unexpectedly stable while having a combination of a strong anionic cleansing detergent, such as a long chain alkyl sulfate, or a partially ethoxylated long chain alkyl sulfate or sulfonate together with a cationic polyethyleneimine and a silicone conditioning agent. The anionic surfactant/cationic polyethyleneimine conditioning agent components are compatible and stable while developing surprisingly high amounts of foam without the problem of anionic surfactant-cationic conditioning agent incompatibility.

BACKGROUND OF THE INVENTION

Soiled human hair is shampooed to remove sebum that is naturally secreted by the head as well as soil and other atmospheric contaminants that accumulate on the hair. Sebum, in particular, accumulates on the hair in a relatively short period of time leaving the hair with a greasy, dirty feel and poor manageability. The most effective shampoos for cleansing the hair for removal of the atmospheric contaminants and sebum, are those that contain high lather synthetic anionic detergents, such as the long chain alkyl sulfates, the partially ethoxylated long chain alkyl sulfates and the long chain sulfonates. These synthetic anionic detergents are very effective for cleansing the hair but, after rinsing with water, leave the hair with a dried touch, usually called "creak" and result in hair, when wet, that is in an extremely tangled and unmanageable after-shampoo condition.

Thoroughly cleansed hair is extremely difficult to comb, in either the wet or dry state because the individual hair fibers tend to snarl, kink, and interlock with each other. Particularly, prior to complete drying of thoroughly cleansed hair, in this after-shampoo stage, the hair is very difficult to comb or brush. Even after complete drying, the thoroughly cleansed hair remains difficult to comb or brush and does not set well. Thoroughly clean, dried hair also has undesirable electrostatic properties in a low humidity atmosphere that causes the hair to "fly away", thereby further reducing the combing or brushing property of the hair. Generally, these above-outlined problems that result from synthetic detergent cleansing of the hair, particularly in the high-lather synthetic anionic detergents, have been alleviated either by the after-shampoo treatment of the hair with hair conditioners, for example, in the form of a hair rinse, or by including hair conditioners directly within the shampoo composition.

After-shampoo hair conditioning compositions are easily formulated but are inconvenient to use because of the necessity of applying the conditioner to the hair in a separate stage, after shampooing. The preparation of a conditioning shampoo has been more difficult because of inherent incompatibility problems between anionic surfactants and the cationic compounds that are good conditioning agents. Contact between an anionic surfactant and a cationic surfactant or cationic polymer produces a precipitate that forms immediately or causes an interaction between the anionic and cationic compounds that significantly reduces their respective cleansing and conditioning properties, and especially a very noticeable severe loss of foam attributed by the anionic cleansing surfactant. The reduction in cleansing and conditioning effectiveness is observed even in compositions wherein the anionic and cationic compounds do not precipitate from the composition but remain in solution or suspension. This incompatibility between an anionic surfactant and a cationic conditioning compound is well recognized by those skilled in the art. For example, Sagarin in *Cosmetics*, Interscience Publishers, Inc., New York, p. 538 (1957), states that anionic and cationic compounds cannot be used in combination because they react to form insoluble salts.

A partial solution to this incompatibility problem in the formulation of conditioning shampoos is exemplified by the following patents that disclose compositions that contain surfactants that are not anionic, e.g., nonionics, amphoterics and zwitterionics together with cationic conditioning compounds: U.S. Pat. No. 3,849,348 to Hewitt; U.S. Pat. No. 3,990,991 to Gerstein; and U.S. Pat. No. 3,822,312 to Sato.

Another problem inherent in formulating a conditioning shampoo is an instability problem that results when water-insoluble conditioning agents are also included in the conditioning shampoo composition, such as the non-volatile silicones that are well recognized in the art as providing a degree of softness to the hair.

Silicones in shampoo compositions have been disclosed in a number of different patents: U.S. Pat. No. 2,826,551, Mar. 11, 1958 to Green; U.S. Pat. No. 3,964,500, Jun. 22, 1976 to Drakoff; U.S. Pat. No. 4,364,837, Dec. 21, 1982 to Pader; British Patent No. 849,433, Sep. 28, 1960 to Woolston; U.S. Pat. No. 4,741,855 to Grote, et al.; U.S. Pat. Nos. 4,788,006 and 4,902,499 to Bolich, Jr., et al. and U.S. Pat. No. 4,704,272 to Oh, et al. The silicones are well known to substantially reduce the foaming of anionic cleansing surfactants.

A particularly difficult problem to solve in silicone-containing conditioning shampoos is that of providing a conditioning shampoo that provides excellent cleansing of the hair while providing high foaming and, at the same time, also has excellent conditioning performance. The capability of providing excellent conditioning, cleansing and foam levels is achieved with the compositions of the present invention. In accordance with one embodiment of the present invention, it has been found that a combination of (1) a cationic (protonated) polyethyleneimine (PEI) in an amount of about 0.01% to about 4% by weight of the composition, preferably about 0.01% to about 1% by weight, together with (2) a cationic oil-soluble, water-dispersible cross-linked quaternary acrylate/acrylamide copolymer (Polyquaternium 32), in an amount of about 0.1% to about 20% based on the total weight of the composition, is stable over long periods of time while providing excellent simultaneous conditioning, cleansing and foaming. Optionally, a number of materials can be included in the conditioning shampoos of the present invention for purposes of thickening and stabilization such as xanthan gum, long chain acyl derivatives, long chain amide oxides or amine oxides, and long chain alkanolamides, as disclosed in U.S. Pat. Nos. 4,788,406; 4,704,272; and 4,741,855, hereby incorporated by reference.

SUMMARY OF THE INVENTION

In accordance with the principles of the present invention, it has been found, surprisingly, that a conditioning shampoo containing an anionic cleansing surfactant, in an amount of about 5% to about 65% by weight, preferably about 5% to about 25% by weight, e.g., ($C_{12}$–$C_{22}$) alkyl sulfate, and/or a long chain ($C_{12}$–$C_{22}$) partially or fully ethoxylated alkyl sulfate, and/or a long chain ($C_{12}$–$C_{22}$) alkyl sulfonate, or alkyl ether sulfonate, and a combination of cationic polymers comprising (1) a cationic (protonated) polyethyleneimine in an amount of about 0.1% to about 4% by weight, preferably about 0.1% to about 1% by weight, and (2) a cationic oil-soluble, water-dispersible, cross-linked quaternary acrylate/acrylamide copolymer (Polyquaternium 32), in an amount of about 0.1% to about 20% by weight of the composition, provides excellent foaming, conditioning and stability, without settling of water-insoluble materials due to anionic-cationic complexing. The composition preferably also includes one or more silicone conditioning agents, and has extended product stability, excellent overall conditioning to human hair, particularly superior wet and dry combing properties, and unexpectedly maintains very high levels of foam.

The compositions of the present invention are stable and do not exhibit the inherent anionic surfactant/cationic polymer, (polyethyleneimine and/or Polyquaternium 32 conditioning agents) incompatibility while providing excellent cleansing, conditioning and foam levels in a conditioning shampoo. It was further surprisingly and unexpectedly found that hair treated with the compositions of the present invention is thoroughly cleansed at high foam levels and exhibits improved physical and cosmetic properties, such as gloss, wet combing, dry combing, thickness, manageability, softness and body.

Therefore, an aspect of the present invention is to provide a hair-treating composition that cleanses the hair and imparts improved physical properties and cosmetic properties to the hair in a single application from a mild conditioning shampoo that develops unexpectedly high foam quantities.

Another aspect of the present invention is to provide a physically stable conditioning shampoo containing an anionic surfactant, and a combination of cationic polymers that provide hair conditioning and composition stability, wherein the composition develops excellent foam levels and can be formulated at room temperature.

Another aspect of the present invention is to provide a new and improved conditioning shampoo containing a strong anionic detergent, such as a long chain alkyl sulfate, long chain alkyl ether sulfate, and/or long chain sulfonate, that is compatible with cationic conditioning agents, and that maintains an unexpectedly high foam level although the composition contains a silicone conditioning agent.

Still another aspect of the present invention is to provide a new and improved conditioning shampoo including about 5% to about 25% of an anionic surfactant; about 0.01% to about 4% of a cationic polyethyleneimine that surprisingly provides composition stability and added conditioning benefits, particularly increased wet and dry combing and reduced static (fly away) for better manageability; and about 0.1% to about 20% of a cationic polymeric conditioning agent (Polyquaternium 32), about 0.01% to about 10% of a silicone conditioning agent, and optionally any known emulsion stabilizer and/or a viscosity increasing agent for added stability of aqueous emulsions, each in an amount of about 0% to about 10% by weight, active, preferably about 0.1% to about 5% by weight.

A further aspect of the present invention is to provide a new and improved method of cleansing and conditioning hair, simultaneously, with a composition containing one or more anionic surfactants; a cationic (protonated) polyethyleneimine having an increased charge density; a cationic acrylate/acrylamide copolymer conditioning agent; and one or more silicone conditioning agents while providing high foam levels, excellent cleansing, excellent conditioning in a stable conditioning shampoo and is capable of being mixed together at room temperature.

Still another aspect of the present invention is to provide a new and improved conditioning shampoo having a pH in the range of about 4 to about 7, preferably about 5 to about 6, including about 5% to about 65% of an anionic surfactant; polyethyleneimine in an amount of about 0.01% to about 4%, preferably about 0.01% to about 1% by weight; optionally about 0.1% to about 20% of a cationic, nitrogen-containing acrylate/acrylamide copolymer conditioning agent; and optionally about 0.5% to about 10% of a cationic silicone conditioning agent.

Another object of the present invention is to provide a new and improved conditioning shampoo having a pH in the range of about 4 to about 7, preferably about 5 to about 6, including about 5% to about 65% of an anionic surfactant; protonated polyethyleneimine in an amount of about 0.01% to about 4%, preferably about 0.01% to about 1% by weight, and having a cationic polymer charge density of at least about 10 milliequivalents per gram, preferably about 15 to about 20 milliequivalents per gram; about 0.1% to about 20% of a cationic acrylate/acrylamide copolymer (Polyquaternium 32) conditioning agent; and about 0.5% to about 10% of a non-volatile silicone material.

The above and other aspects and advantages of the present invention will become apparent from the following detailed description of the preferred embodiments.

DETAILED DESCRIPTION OF THE PREFERRED EMBODIMENTS

The aqueous conditioning shampoo compositions of the present invention generally include water in an amount of about 60% to about 80–90% by weight; an anionic surfactant preferably in an amount of about 5% to about 25% by weight of the composition; a poleythyleneimine in an amount of about 0.01% to about 4%, preferably about 0.01% to about 1% by weight; optionally a silicone conditioning agent in an amount of about 0.1% to about 10% by weight of the composition; and Polyquaternium 32, a cationic conditioning agent, in an amount of about 0.1% to about 20% by weight of the composition.

The conditioning shampoo of the present invention provides the hair with improved physical and cosmetic conditioning properties, such as gloss, thickness, softness, and manageability, including excellent wet and dry combing properties and body simultaneously with excellent cleansing at high foam levels in a mild conditioning shampoo. As will be demonstrated more fully hereinafter, it is surprising and unexpected that the composition of the present invention, including an anionic cleansing detergent, and a cationic conditioning compound is able to provide the demonstrated cleansing at such a high foam level in a stable composition containing a silicone conditioning agent.

The anionic cleansing surfactant used in the composition and method of the present invention can be any of the anionic surfactants known or previously used in the art of hair shampoos. An anionic cleansing surfactant should be included in the composition of the present invention to effectively cleanse the hair and generates a high, stable foam level that consumers equate with cleaning efficiency. While nonionic and amphoteric surfactants have not been as effective in cleansing the hair and do not provide the high foam level desired by consumers, surprisingly, it has been found that the composition of the present invention provides excellent foam levels with the less strong anionic cleansing detergents or with the strong anionic detergents at levels generally below about 9% by weight of the composition, particularly when the foam level is boosted with one or more common foam boosters, such as a betaine or other foam booster. Optionally, nonionic amphoteric and/or zwitterionic surfactants can be included in the compositions of the present invention in addition to one or more anionic surfactants, to help stabilize foam, to provide a suitable viscosity, or to give other functional or esthetic properties to the composition.

Usually, the anionic cleansing surfactant includes a hydrophobic moiety, such as a carbon chain including from about eight carbon atoms to about 30 carbon atoms, and particularly from about 12 carbon atoms to about 22 carbon atoms and further includes a hydrophilic moiety, such as a sulfate, sulfonate, carbonate, phosphate or carboxylate. Often, the hydrophobic carbon chain is etherified, such as with ethylene oxide or propylene oxide, to impart a particular physical property, such as increased water-solubility or reduced surface tension, to the anionic cleansing surfactant.

Suitable anionic cleansing surfactants include, but are not limited to, compounds in the classes known as alkyl sulfates, alkyl ether sulfates, alkyl sulfonates, alkyl ether sulfonates, sulfate esters of an alkylphenoxy polyoxyethylene ethanol, alpha-olefin sulfonates, beta alkyloxy alkene sulfonates, alkyl arylsulfonates, alkyl carbonates, alkyl ether carboxylates, fatty acids, succinamates, sulfosuccinates, sarcosinates, octoxynol or nonoxynol phosphates, taurates, fatty taurides, sulfated monoglycerides, fatty acid amino polyoxyethylene sulfates and isothienates; or combinations thereof. Many additional anionic cleansing surfactants are described in McCUTCHEON'S DETERGENTS AND EMULSIFIERS, 1989 ANNUAL published by McCutcheon's Division MC Publishing Company, herein incorporated by reference. Usually, the anionic cleansing surfactant is present in the composition as a neutralized salt in the form of a sodium, potassium, lithium, ammonium. alkylammonium or hydroxyalkylammonium salt, wherein the alkyl moiety includes from one to about three carbon atoms.

Exemplary anionic cleansing surfactants that are useful in the composition and method of the present invention include, but are not limited to, the ammonium, monoethanolamine, diethanolamine, triethanolamine, isopropylamine, sodium, potassium, lithium, or magnesium salts of lauryl sulfate, dodecylbenzenesulfonate, lauryl sulfosuccinate, lauryl ether sulfate, lauryl ether carboxylate, lauryl sarcosinate, cocomethyl tauride, and sulfosuccinate half ester amide; or combinations thereof. Also useful are the zwitterionic betaines, e.g., cocamdopropyl betaine, cocamidopropyl hydroxysultaine, and the like; and the anionic carboxylate cleansing detergents, such as $C_{11}$–$C_{15}$ Pareth-7 carboxylic acid, $C_{11}$–$C_{15}$ Pareth-9, $C_{11}$–$C_{15}$ Pareth-12, $C_{11}$–$C_{15}$ Pareth-20, $C_{11}$–$C_{15}$ Pareth-30, $C_{11}$–$C_{15}$ Pareth-40, $C_{11}$–$C_{21}$ Pareth-10, $C_{12}$–$C_{13}$ Pareth-5 carboxylic acid, $C_{12}$–$C_{15}$ Pareth-2 phosphate, $C_{12}$–$C_{15}$ Pareth-7 carboxylic acid, $C_{12}$–$C_{15}$ Pareth-9, $C_{12}$–$C_{15}$ Pareth-12, $C_{14}$–$C_{15}$ Pareth-13, $C_{22}$–$C_{24}$ Pareth-33, cocaminobutyric acid, cocaminopropionic acid, coceth-7 carboxylic acid, cocoamphodipropionic acid, coconut acid, deceth-7 carboxylic acid, hydrogenated coconut acid, hydrogenated menhaden acid, hydrogenated tallow acid, hydroxystearic acid, isostearic acid, lanolin acid, lauraminopropionic acid, laureth-5 carboxylic acid, laureth-10 carboxylic acid, lauroamphodipropionic acid, linoleic acid, linolenic acid, linseed acid, MEA-laureth-6-carboxylate, myristaminopropionic acid, palmitic acid, sodium $C_{12}$–$C_{15}$ Pareth-6 carboxylate, sodium $C_{12}$–$C_{15}$ Pareth-7 carboxylate, sodium ceteth-13 carboxylate, sodium isosteareth-6 carboxylate, sodium isosteareth-11 carboxylate, sodium laureth-13 carboxylate, sodium trideceth-7 carboxylate, sodium trideceth-12 carboxylate, trideceth-4 carboxylic acid, trideceth-7 carboxylate acid, trideceth-15 carboxylic acid, and trideceth-19 carboxylic acid.

The following low-irritation surfactants are particularly useful in formulating a "baby" shampoo having high performance in terms of foam level and cleansing while achieving exceptional mildness:

ANIONICS

Disodium Laureth Sulfosuccinate;
Disodium Lauroamido MEA Sulfosuccinate;
Disodium Ricinoleamido MEA Sulfosuccinate;
Ceteareth-25-Carboxylic Acid;
Trideceth-7-Carboxylic Acid;
Pareth-25-6-Carboxylic Acid;
Trideceth-4-Carboxylic Acid;
Trideceth-19-Carboxylic Acid;
Sodium Trideceth-12-Carboxylate;

Sodium Ceteth-13-Carboxylate;
Laureth-5-Carboxylic Acid (SANDOPAN® LA8);
Sodium Laureth-13-Carboxylate;
Sodium Oleth-13-Carboxylate;
Sodium Ceteareth-5-Carboxylate;
Sodium Ceteareth-9-Carboxylate;
Isosteareth-6-Carboxylic Acid; and
Isosteareth-11-Carboxylic Acid.

NONIONICS

PEG 30 Glyceryl Mono Cocoate;
PEG 78 Glyceryl Mono Cocoate;
PEG 82 Glyceryl Mono Tallowate;
PEG 200 Glyceryl Mono Tallowate; and
PEG 20 Glyceryl Mono Tallowate.

AMPHOTERICS

Cocampho-Carboxyglycinate (VARION® 2C);
Lauroampho-Carboxyglycinate (VARION® 2L);
Cocamidopropyl Betaine; and
Cocamidopropyl Hydroxysultaine (VARION® CAS).

The polyethyleneimine(s) contained in the conditioning shampoos of the present invention generally have the formula $(CH_2CH_2NH)_n$ wherein n has an average value of about 5 to about 2500. Specific examples of polyethyleneimines are PEI-7; PEI-15; PEI-30; PEI-45; PEI-1000; PEI-1500; and PEI-2500, wherein the integer following the PEI corresponds to the value of n in the formula above.

Surprisingly, protonated polyethyleneimines, together with the cationic Polyquaternium 32, provide excellent stability while achieving additional conditioning benefits from the protonated polyethyleneimine. The polyethyleneimines can be obtained protonated with any suitable acid at a pH below about 7.0, or the polyethyleneimines can be protonated in-situ (during mixing of the composition with an acid, e.g., citric acid) by adding sufficient acid that is free to protonate the polyethyleneimine. The molecular weight of the polyethyleneimine is not critical and can be any molecular weight commercially available, e.g., protonated polyethyleneimines available from BASF Corporation having a weight average molecular weight in the range of about 700 to about 70,000. The ability to provide a conditioning shampoo that has excellent conditioning benefits, as well as excellent foaming and stability, has been a long-felt need in the conditioning shampoo art. The conditioning shampoos of the present invention solve this long-felt need by including a protonated polyethyleneimine and a cationic acrylate/acrylamide co-polymer, particularly Polyquaternium 32. The structure of protonated polyethyleneimine is as follows:

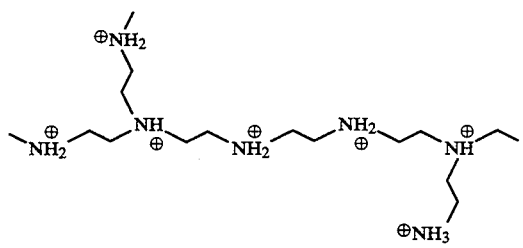

The preferred protonated polyethyleneimines have a ratio of primary:secondary:tertiary nitrogen atoms of about 1:2:1, respectively.

The emulsified conditioning shampoo of the present invention also includes a cationic conditioning agent, such as a SALCARE SC92 acrylate/acrylamide co-polymer conditioning agent of Allied Colloids (POLYQUATERNIUM 32) as disclosed in our parent application Ser. No. 07/719,818 filed Jun. 24, 1991, hereby incorporated by reference.

To achieve the full advantage of the present invention, an optional foam booster, in an amount of about 0.1% to about 20% by weight of the composition, is included in the composition to aid in the formation of copious amount of foam. Suitable foam boosters include one or more of the following:

| | |
|---|---|
| Capramide DEA | Disodium Isostearyl Sulfosuccinate |
| Cetearyl Alcohol | Hydrogenated Tallow Amine Oxide |
| Cetyl Alcohol | Hydroxyethyl Hydroxypropyl $C_{12}$–$C_{15}$ Alkoxypropylamine Oxide |
| Cetyl Betaine | Hydroxyethyl Stearamide-MIPA |
| Cocamide | Isopropyl Stearate |
| Cocamide DEA | Isostearamidopropylamine Oxide |
| Cocamide MEA | Isostearamidopropyl Morpholine Oxide |
| Cocamide MIPA | Lauramide |
| Cocamidoethyl Betaine | Lauramide DEA |
| Cocamidopropylamine Oxide | Lauramide MEA |
| Cocamidopropyl Betaine | Lauramide MIPA |
| Cocamidopropyl Hydroxysultaine | Lauramidopropylamine Oxide |
| Cocamine Oxide | Lauramidopropyl Betaine |
| Cocoamphodipropionic Acid | Lauramine Oxide |
| Coco-Betaine | Lauryl Alcohol |
| Coco-Morpholine Oxide | Lauryl Betaine |
| Coconut Alcohol | Lauryl Sultaine |
| Coco/Oleamidopropyl Betaine | Myristamide DEA |
| Coco-Sultaine | Myristamide MEA |
| Cocoyl Hydroxyethyl Imidazoline | Myristamide MIPA |
| Cocoyl Sarcosinamide DEA | Myristamidopropylamine Oxide |
| DEA-Cocoamphodipropionate | Myristamidopropylamine Betaine |
| DEA-Lauraminopropionate | Myristamine Oxide |
| Decylamine Oxide | Myristaminoproionic Acid |
| Decyl Betaine | Myristyl Alcohol |
| Dihydroxyethyl $C_8$–$C_{10}$ Alkoxypropylamine Oxide | Myristyl Betaine |
| Dihydroxyethyl $C_9$–$C_{11}$ Alkoxypropylamine Oxide | Oleamidopropylamine Oxide |
| Dihydroxyethyl $C_{12}$–$C_{15}$ Alkoxypropylamine Oxide | Oleamidopropyl Betaine |
| Dihydroxyethyl Cocamine Oxide | Oleamidopropyl Hydroxysultaine |
| Dihydroxyethyl Stearamine Oxide | Oleamine Oxide |
| Dihydroxyethyl Tallowamine Oxide | Oleyl Betaine |
| | Palmamide DEA |
| Palmamide MEA | PEG-5 Lauramide |
| Palmamide MIPA | PEG-6 Lauramide |
| Palmamidopropyl Betaine | PEG-3 Lauramine Oxide |
| Palmitamide DEA | Sodium Cocoamphoacetate |
| Palmitamide MEA | Sodium Cocoamphopropionate |
| Palmitamidopropylamine Oxide | Sodium Lauraminopropionate |
| Palmitamidopropyl Betaine | Sodium Lauroamphopropionate |
| Palmitamine Oxide | Sodium Lauroyl Sarcosinate |
| Palm Kernel Alcohol | Sodium Myristoamphoacetate |
| Palm Kernelamide DEA | Sodium Myristoyl Sarcosinate |

| | |
|---|---|
| Palm Kernelamide MEA | Stearyl Alcohol |
| Palm Kernelamide MIPA | TEA-Hydrogenated Tallow Glutamate |
| Peanutamide MEA | TEA-Lauraminopropionate |
| Peanutamide MIPA | TEA-Myristaminopropionate |
| PEG-6 Cocamide | Undecylenamide DEA |
| PEG-3 Lauramide | Undecylenamide MEA |
| | Undecylenamidopropylamine Oxide |

One or more zwitterionic detergents, such as a betaine, in an amount of about 5% to about 25% by weight of the composition aids in stabilizing the composition but generally is not necessary to achieve a stable composition. Suitable betaines include, for example:

| | |
|---|---|
| Betaine | Myristamidopropyl Betaine |
| Cetyl Betaine | Myristyl Betaine |
| Cocamidoethyl Betaine | Oleamidopropyl Betaine |
| Cocamidopropyl Betaine | Oleamidopropyl Hydroxysultaine |
| Cocamidopropyl Hydroxysultaine | Oleyl Betaine |
| Coco-Betaine | |
| Coco/Oleamidopropyl Betaine | Palmamidopropyl Betaine |
| | Palmitamidopropyl Betaine |
| Coco-Sultaine | Ricinoleadmidopropyl Betaine |
| Decyl Betaine | Stearamidopropyl Betaine |
| Hydrogenated Tallow Betaine | Stearyl Betaine |
| Isostearamidopropyl Betaine | Tallowamidopropyl Betaine |
| Lauramidopropyl Betaine | Tallowamindopropyl Hydroxysultaine |
| Lauryl Betaine | Wheat Germamidopropyl Betaine |
| Lauryl Sultaine | |

Other compounds useful for composition stabilization, in an amount of about 0.1% to about 10% by weight of the composition include any one or more of the following:

| | |
|---|---|
| Acetylated Glycol Stearate | Maltodextrin |
| Aluminum Caprylate | Methoxy PEG-22/Dodecyl Glycol Copolymer |
| Aluminum Dilinoleate | Methylcellulose |
| Aluminum Distearate | Microcrystalline Cellulose |
| Aluminum Isostearates/Laurates/Palmitates | Microcrystalline Wax |
| Aluminum Isostearates/Laurates/Stearates | Montmorillonite |
| Aluminum Isostearates/Myristates | Myristyl Alcohol |
| Aluminum Isostearates/Palmitates | Ozokerite |
| Aluminum Isostearates/Stearates | Pectin |
| Aluminum Lanolate | PEG-2M |
| Aluminum Myristates/Palmitates | PEG-5M |
| Aluminum Stearate | PEG-7M |
| Aluminum Stearates | PEG-9M |
| Aluminum Tristearate | PEG-14M |
| Beeswax | PEG-20M |
| Bentonite | PEG-23M |
| $C_9$–$C_{11}$ Alcohols | PEG-45M |
| $C_{12}$–$C_{13}$ Alcohols | PEG-90M |
| $C_{12}$–$C_{15}$ Alcohols | PEG-115M |
| $C_{12}$–$C_{16}$ Alcohols | PEG-22/Dodecyl Glycol Copolymer |
| $C_{14}$–$C_{15}$ Alcohols | PEG-45/Dodecyl Glycol Copolymer |
| $C_{15}$–$C_{18}$ Glycol | Polyacrylic Acid |
| Calcium Carrageenan | Polyethylene |
| Calcium Stearate | Polyvinyl Acetate |
| Carbomer 910 | Potassium Alginate |
| Carbomer 934 | Potassium Carrageenan |
| Carbomer 934P | PVM/MA Copolymer |
| Carbomer 940 | PVP/VA Copolymer |
| Carbomer 941 | Saccharated Lime |
| Carboxymethyl Hydroxyethylcellulose | Sodium Acrylate/Vinyl Alcohol Copolymer |
| Carboxymethyl Hydroxypropyl Guar | Sodium $C_4$–$C_{12}$ Olefin/Maleic Acid Copolymer |
| Carrageenan | Sodium Carboxymethyl Dextran |
| Cellulose Gum | Sodium Carrageenan |
| Ceresin | Sodium Cellulose Sulfate |
| Cetearyl Alcohol | Sodium Polymethacrylate |
| Cetyl Alcohol | Sodium Polynaphthalene Sulfonate |
| Cholesterol | Sodium Polystyrene Sulfonate |
| Coconut Alcohol | Stearyl Alcohol |
| Ethylene/Acrylate Copolymer | Stearylvinyl Ether/Maleic Anhydride Copolymer |
| Ethylene/Vinyl Acetate Copolymer | Styrene/Maleic Anhydride Copolymer |
| Guar Gum | Synthetic Beeswax |
| Hydroxybutyl Methylcellulose | Synthetic Wax |
| Hydroxyethylcellulose | |
| Hydroxyethyl Ethylcellulose | Tallow Alcohol |
| Hydroxypropylcellulose | Tragacanth Gum |
| Hydroxypropyl Guar | Tridecyl Alcohol |
| Hydroxypropyl Methylcellulose | Xanthan Gum |
| Isopropyl Ester of PVM/MA Copolymer | |
| Karaya Gum | |
| Lanolin | |
| Lanolin Alcohol | |
| Lauryl Alcohol | |
| Locust Bean Gum | |

Other common cosmetic components and additives that can be incorporated into the conditioning shampoos of the present invention, as long as the basic properties of conditioning, cleansing and high foam levels are not adversely affected include, for example, fragrances, dyes, hair colorants, opacifiers, pearlescing agents, dandruff control agents, hydrotropes, foam stabilizers, solubilizers, preservatives, water softening agents, acids, bases, buffers and the lie. These optional components and additives usually will be present in weight percentages of less than about 2% each, and from about 5% to about 10% by weight in total.

The vehicle of the hair-treating composition is generally predominantly water, but organic solvents also can be used in order to help solubilize compounds that are not sufficiently soluble in water. Suitable solvents include the lower alcohols like ethyl alcohol and isopropyl alcohol; polyols like glycerol; glycols or glycol ethers, like 2-butoxyethanol, ethylene glycol, ethylene glycol monoethyl ether, propylene glycol and diethylene glycol monoethyl ether or monoethyl ether; and mixtures thereof. These non-aqueous solvents can be present in the hair-treating composition of the present invention in an amount from about 1% to 100% by weight and, in particular, from about 5% to about 50% by weight, relative to the total weight of the carrier vehicle in the composition.

The conditioning shampoos of the present invention also can be thickened, for example, with sodium alginate; guar gum; xanthan gum; gum arabic; cellulose derivatives such as methylcellulose, hydroxyethylcellulose, hydroxypropylmethylcellulose and carboxymethylcellulose; and various polymeric thickeners, such as polyacrylic acid derivatives. These thickeners are present in an amount ranging from about 0.1% to about 5%, and preferably from about 0.25% to about 1%, by weight relative to the total weight of the composition.

If instability of the composition is a problem, the composition also can include a suspending agent for the conditioning agent or other water-insoluble material, in an amount of about 0.5% to about 10%, by total weight of the composition. Suitable suspending agents are for example, distearyl amate (distearyl phthalamic acid); fatty acid alkanolamides; esters of polyols and sugars; polyethylene glycols; the ethoxylated or propoxylated alkylphenols; ethyoxylated or propoxylated fatty alcohols; and the condensation products of ethylene oxide with long chain amides. These suspending agents, as well as numerous others not cited herein, are well known in the art and are fully described in literature, such as McCUTCHEON'S DETERGENTS AND EMULSIFIERS, 1989 Annual, published by McCutcheon Division, MC Publishing Co.

The conditioning shampoos also can include other emulsifiers, inorganic salts, humectants and similar materials to provide esthetic properties and desirable physical properties to the composition. Generally, such optional ingredients are present in weight percentages ranging from about 0.1% to about 10% each, and from about 0.1% to about 20% in total, relative to the total weight of the composition.

For example, representative nonionic surfactants that can be included in the hair-treating composition of the present invention include esters of polyols and sugars; the polyethoxylated and/or polypropoxylated alkylphenols; and the condensation products of ethylene oxide with long chain amides. All these nonionic surfactants, as well as numerous others not cited here, are well known in the art and are fully described in the literature.

The compositions of the present invention can be relatively viscous dispersions that are stable to phase separation at a temperature of about 20° C. to about 25° C. for a period of time of at least 24 hours after preparation, and typically are stable to phase separation indefinitely at such temperatures. The compositions of the present invention usually are emulsions that are stable to phase separation at a temperature of about 25° C. for a period of about 24 hours after preparation. The emulsions should demonstrate sufficient stability to phase separation at temperatures normally found in commercial product storage and shipping to remain unaffected for period of one year or more.

The following examples illustrate various conditioning shampoos made in accordance with the present invention:

EXAMPLES 1-3

|  | 1 WT. % | 2 WT. % | 3 WT. % |
| --- | --- | --- | --- |
| 1. Water | 30.00 | 30.00 | 30.00 |
| 2. Polyvinylpyrrolidone (stabilizing agent) | 1.00 | 1.00 | 1.00 |
| 3. Polyethyleneimine (Polymin G-35 BASF) wt. av. M.W - 1,700 as measured by GPC (conditioning and stability) | 1.00 | 1.00 | 1.00 |
| 4. Acrylate/acrylamide copolymer (Allied Colloids Salcare SC92) (50% in mineral oil) | 1.00 | 1.00 | 1.00 |
| 5. Citric Acid (pH adjustment) | 1.80 | 1.80 | 1.80 |
| 6. Cocamide DEA (foam booster) | 1.00 | 1.00 | 1.00 |
| 7. Surfactant blend (cleansing) (a) ALES (1 mole ethoxylation) (8.0%) (b) lauramide DEA (3.5%) (c) ammonium xylene sulfonate (0.5%) (d) water q.s. | 35.00 | 35.00 | 35.00 |
| 8. Silicone blend 33% SE 30 67% SF96-350 (conditioners) | 0.65 | 0.65 | 0.65 |
| 9. Water | 8.00 | 10.00 | 9.50 |
| 10. Sodium lauryl sulfate (cleansing, foam) | 15.00 | 15.00 | 15.00 |
| 11. Cocamidopropyl Hydroxysultaine (40%) (VARION ® CAS) (amphoteric surfactant) | 4.00 | 2.00 | 2.00 |
| 12. Cocamide DEA (foam booster) | 1.00 | 1.00 | 1.00 |
| 13. Kathon CG (preservative) | 0.05 | 0.05 | 0.05 |
| 14. Glydant (preservative) | 0.20 | 0.20 | 0.20 |
| 15. Fragrance | 0.30 | 0.30 | 0.30 |
| pH | 4.2 | 4.4 | 4.2 |
| Viscosity | 2,000 cps. | 2,250 cps. | 2,150 cps. |

Mixing Procedure Examples 1-3

Add the polyvinylpyrrolidone (#2) to water (#1) with high agitation. Then add the polyethyleneimine (#3) and continue mixing. Then add the acrylate/acrylamide copolymer (#4) and mix until homogeneous (lump free). Then add the citric acid (#5), the cocamide DEA (#6), the surfactant blend (#7) and the silicone blend (#8). Into a separate container add the sodium lauryl sulfate (#10) to water (#9) and then add the contents of the separate container to the mixture of (#1) through (#8), with agitation. Then add the VARION ® CAS (#13), the glydant (#14) and the fragrance (#15).

EXAMPLE 4

|  | WT. % |
| --- | --- |
| 1. Water | 59.05 |
| 2. Polyethyleneimine (Polymin G35, BASF) (conditioning and stability) | 0.10 |
| 3. Acrylate/acrylamide copolymer Allied Colloids D.P. 64297C (50% in mineral oil) | 2.50 |
| 4. SURFODONE ® QSP (polylauryl pyrrolidone) polymeric emulsion stabilizer | 0.50 |
| 5. SANDOPAN ® LA 8 (carboxylate surfactant) | 7.00 |

-continued

| | WT. % |
|---|---|
| 6. SURFINE ® WNT A (carboxylate surfactant) | 7.00 |
| 7. KOH (50%) | 0.60 |
| 8. Cocamidopropyl Hydroxysultaine (40%) (VARION ® CAS) (amphoteric surfactant) | 15.00 |
| 9. $C_{16-18}$ amine oxide (40%) (SCHERCAMOX ® CMA) | 2.00 |
| 10. GLUCAMATE ® DOE 120* (thickener) | 0.50 |
| 11. Color, fragrance, preservative pH = 5.19 Viscosity (25° C.) = 3,000 cps. | q.s. |

*polyethylene glycol diester of methyl glucose and oleic acid with an average of 120 moles of ethylene oxide.

EXAMPLE 5

| | WT. % |
|---|---|
| 1. Water | 19.50 |
| 2. Polyethyleneimine (Polymin P, BASF) (conditioning and stability) | 0.50 |
| 3. Acrylate/acrylamide copolymer Allied Colloids D.P. 64297C (50% in mineral oil) | 2.00 |
| 4. Cocamidopropyl Hydroxysultaine (40%) (VARION ® CAS) (amphoteric surfactant) | 15.00 |
| 5. Cocamide DEA (foam booster) | 4.00 |
| 6. SANDOPAN ® LA 8 (carboxylate surfactant) | 15.00 |
| 7. Water | 42.05 |
| 8. KOH (50%) | 1.40 |
| 9. Perfume | 0.30 |
| 10. Glydant | 0.20 |
| 11. Kathon CG pH - 5.0 Viscosity (25° C.) = 2,000 cps. | 0.05 |

Mixing Procedure Example 5

Add the sultaine (#4), the polyethyleneimine (#2), and the acrylate/acrylamide copolymer (#3) to water (#1) with mixing (1 hour). Then add the Cocamide DEA (#5) and mix until homogeneous (lump free). Into a separate container, add the SANDOPAN ® carboxylate surfactant (#6) to water (#7) followed by the KOH (#8) addition and then mix all items (#1) through (#8). The perfume (#9), glydant (#10) and Kathon CG (#11) then are added.

EXAMPLE 6

| | WT. % |
|---|---|
| 1. Water | 35.50 |
| 2. Polyethyleneimine (POLYMIN WATERFREE, BASF) (conditioning and stability) | 0.50 |
| 3. SURFADONE ® QSP (polylauryl pyrrolidone) polymeric emulsion stabilizer | 0.60 |
| 4. Acrylate/acrylamide copolymer Allied Colloids D.P. 65780E (50% mineral oil) | 3.00 |
| 5. Surfactant Blend: (a) ALES (1 mole ethoxylation) (4.5%) (b) lauramide DEA (2.5%) (c) ammonium xylene sulfonate (0.6%) (d) water q.s. | 20.00 |
| 6. KOH (50%) | 0.50 |
| 7. SANDOPAN ® LA 8 (carboxylate surfactant) | 15.00 |
| 8. KOH | 1.00 |
| 9. Cocamidopropyl Hydroxysultaine (40%) (VARION ® CAS) (amphoteric surfactant) | 10.00 |
| 10. Perfume | 0.50 |
| 11. Glydant | 0.20 |
| 12. Kathon CG | 0.05 |
| 13. Cold pearl mix | 3.00 |
| 14. Cocamide DEA FO (foam booster) | 3.00 |
| 15. Water, color | 7.15 |

Mixing Procedure Example 6

Add (#2) and (#3) in (#1), mix until no lumps, then add (#4) and mix until a soft gel is formed in about 40 minutes, avoid aeration;

Add (#5), mix for 5 minutes (precipitation is observed);

Add (#6) and (#7) and mix for 5 minutes;

Add (#8), mix until product is uniform (pH 4.5);

Add (#9), gradually, add (#10), (#11), (#12), (#13), (#14) and (#15).

pH 4.5

ADD KOH (50%)—0.6% to pH 5.13

FINAL pH = 5.13

Viscosity (25° C.) = 6,300 cps.

To show that the compositions of the present invention are compatible with a relatively low percentage of sodium lauryl ether (1 mole of ethoxylation) sulfate (SLES), Example 7 incorporates 5% by weight of sodium lauryl ether sulfate (1 mole of ethoxylation) (SLES) together with about 15% of other, mild carboxylate anionic surfactants.

EXAMPLE 7

| | WT. % |
|---|---|
| 1. Water, Soft | 20.72 |
| 2. Polyethyleneimine (POLYMIN PS, BASF) (conditioning and stability) | 2.00 |
| 3. SURFODONE ® QSP (polylauryl pyrrolidone) polymeric emulsion stabilizer | 0.38 |
| 4. Acrylate/acrylamide copolymer Allied Colloids D.P. 65789E (50% in mineral oil) | 1.90 |
| 5. Water | 22.75 |
| 6. SANDOPAN ® LA 8 (90%) (carboxylate surfactant) | 15.00 |
| 7. KOH (50%) | 1.50 |
| 8. SLES (25%) | 20.00 |
| 9. Cocamidopropyl Hydroxysultaine (40%) (VARION ® 2L) (amphoteric surfactant) | 10.00 |
| 10. Cocamide DEA (foam stabilizer) | 3.00 |
| 11. Perfume | 0.50 |
| 12. Kathon CG | 0.05 |
| 13. Clydant | 0.20 |
| 14. $C_{16-18}$ amide oxide (40%) SHERCOMOX ® CMA pH = 6.0 Viscosity (25° C.) = 8,500 cps. | 2.00 |

Mixing Procedure Example 7

Add (#2) to (#3) to (#1), mix well and add (#4), mix until soft gel is formed.

Add remaining ingredients. Allow 5 minutes of mixing for each addition.

What is claimed is:

1. A conditioning shampoo for cleansing and conditioning hair while maintaining foam comprising water, an anionic cleansing surfactant in an amount of about 5% to about 65% by weight; a cationic polyethyleneimine in an amount of about 0.01% to about 4% by weight; and a cationic oil-soluble, water-dispersible, cross-linked acrylate/acrylamide copolymer conditioning agent in an amount of about 0.1% to about 20% by weight.

2. The composition of claim 1, wherein the anionic surfactant is a carboxylate surfactant.

3. The composition of claim 1 further including a long chain ($C_{12}$–$C_{22}$) amine oxide emulsion stabilizer in an amount of about 0.1% to about 5% based on the weight of the composition.

4. The composition of claim 1 having a pH of about 4.5 to about 7.5.

5. The composition of claim 1, wherein the composition includes a viscosity increasing agent in an amount of about 0.1% to about 10% by weight for raising the viscosity of the composition to at least about 3,000 centipoises.

6. The composition of claim 1 further including a zwitterionic detergent in an amount of about 5% to about 15% by weight of the composition.

7. The composition of claim 1, wherein the composition includes a betaine surfactant in an amount of about 5% to about 25% by weight of the composition.

8. The composition of claim 7, wherein the betaine surfactant is cocamidopropyl hydroxysultaine.

9. The composition of claim 1, further including a silicone conditioning agent in an amount of about 0.1% to about 10% by weight of the composition.

10. The composition of claim 1, wherein the composition includes less than about 9% by weight of an anionic surfactant selected from the group consisting of a long chain ($C_{12}$–$C_{22}$) alkyl sulfate, a long chain ($C_{12}$–$C_{22}$) alkyl ether sulfate; a long chain ($C_{12}$–$C_{22}$) alkyl sulfonate; and a long chain ($C_{12}$–$C_{22}$) alkyl ether sulfonate.

11. The composition of claim 1, wherein the polyethyleneimine has a cationic polymer charge density of at least about 10 milliequivalents per gram.

12. The composition of claim 11, wherein the polyethyleneimine has a cationic polymer charge density in the range of about 15 to about 20 milliequivalents per gram.

13. The composition of claim 1, wherein the polyethyleneimine has a weight average molecular weight in the range of about 700 to about 70,000.

14. A method of cleansing and conditioning hair, simultaneously while maintaining foam and excellent cleansing in a shampoo composition comprising contacting the hair with a conditioning shampoo comprising water, an anionic cleansing surfactant in an amount of about 5% to about 65% by weight, a protonated polyethyleneimine in an amount of about 0.01% to about 4% by weight and a cationic oil-soluble, water-dispersible, cross-linked acrylate/acrylamide copolymer conditioning agent in an amount of about 0.1% to about 20% by weight.

15. The method of claim 14, wherein the conditioning shampoo includes an anionic carboxylate surfactant.

16. The method of claim 14, wherein the conditioning shampoo further includes a long chain ($C_{12}$–$C_{22}$) amine oxide emulsion stabilizer in an amount of about 0.1% to about 5% based on the weight of the composition.

17. The method of claim 14, wherein the conditioning shampoo further includes a viscosity increasing agent in an amount of about 0.1% to about 10% by weight for raising the viscosity of the composition to at least about 3,000 centipoises.

18. The method of claim 15, wherein the conditioning shampoo includes a zwitterionic detergent in an amount of about 5% to about 15% by weight of the composition.

19. The method of claim 14, wherein the conditioning shampoo includes a betaine surfactant in an amount of about 5% to about 25% by weight of the composition.

20. The method of claim 19, wherein the betaine surfactant is cocamidopropyl hydroxysultaine.

21. The method of claim 19, wherein the conditioning shampoo further includes a silicone conditioning agent in an amount of about 0.1% to about 10% by weight of the conditioning shampoo.

* * * * *

UNITED STATES PATENT AND TRADEMARK OFFICE
CERTIFICATE OF CORRECTION

PATENT NO. : 5,417,965
DATED : MAY 23, 1995
INVENTORS : JANCHITRAPONVEJ, ET AL.

It is certified that error appears in the above-identified patent and that said Letters Patent is hereby corrected as shown below:

Column 5, lines 10-11, "a poleythyleneimine" should be -- a polyethyleneimine --;

Column 6, line 14, "ammonium." should be -- ammonium, --;

Column 6, lines 43-44, "linoleic acid, linoleic acid, linseed acid," should be -- linoleic acid, linseed acid, --;

Column 9, line 32, "Tallowamindopropyl" should be -- Tallowamidopropyl --;

Column 9, line 65, "$C_9$-$C_{11}$ Alcohols" should be -- $C_9$-$C_{11}$ Alcohols --;

Column 11, line 20, "ethyoxylated" should be -- ethoxylated --; and

Column 16, line 33, "of claim 15," should be -- of claim 14 --.

Signed and Sealed this

Seventh Day of May, 1996

Attest:

BRUCE LEHMAN

Attesting Officer    Commissioner of Patents and Trademarks